US007647190B2

(12) United States Patent
Uemura et al.

(10) Patent No.: US 7,647,190 B2
(45) Date of Patent: Jan. 12, 2010

(54) ANALYZING SYSTEM, DIAGNOSTIC INFORMATION PROCESSING DEVICE, AND COMPUTER PROGRAM PRODUCT THEREOF

(75) Inventors: Mamoru Uemura, Kobe (JP); Kenichi Takahashi, Osaka (JP); Yasutaka Arino, Fukuoka (JP); Akinobu Seko, Kobe (JP); Yuji Takano, Fukuoka (JP)

(73) Assignee: Sysmex Corporation, Hyogo (JP)

( * ) Notice: Subject to any disclaimer, the term of this patent is extended or adjusted under 35 U.S.C. 154(b) by 454 days.

(21) Appl. No.: 11/491,274

(22) Filed: Jul. 24, 2006

(65) Prior Publication Data

US 2007/0038406 A1   Feb. 15, 2007

(30) Foreign Application Priority Data

Jul. 25, 2005   (JP)   ............................. 2005-214246

(51) Int. Cl.
  *G05B 15/00*   (2006.01)
  *G06F 17/00*   (2006.01)
(52) U.S. Cl. .................... 702/31; 73/863; 73/863.01; 436/8; 436/43; 700/90; 702/1; 702/22; 702/30; 702/187
(58) Field of Classification Search ............... 73/1.03, 73/1.01, 1.02, 19.01, 19.02, 53.01, 61.41, 73/61.43, 61.59, 863, 863.01, 864.81; 250/252.1, 250/306, 307; 356/36, 39, 40, 41; 435/283.1, 435/287.1, 287.3; 436/8, 43, 46, 47; 700/1, 700/90; 702/1, 22, 23, 24, 25, 26, 27, 28, 702/29, 30, 31, 32, 85, 87, 88, 104, 105, 702/127, 187, 188, 189
See application file for complete search history.

(56) References Cited

U.S. PATENT DOCUMENTS

| 3,526,125 | A | * | 9/1970 | Gilford et al. ............... 73/64.56 |
| 3,533,744 | A | * | 10/1970 | Unger .......................... 436/63 |
| 3,536,449 | A | * | 10/1970 | Astle .......................... 436/179 |
| 4,585,007 | A | * | 4/1986 | Uchigaki et al. ............ 600/363 |
| 2005/0003554 | A1 | * | 1/2005 | Brasseur ..................... 436/172 |
| 2005/0102166 | A1 | | 5/2005 | Tohma |
| 2005/0131734 | A1 | | 6/2005 | Sugiyama |

FOREIGN PATENT DOCUMENTS

JP   4-38467 A   2/1992

* cited by examiner

*Primary Examiner*—Edward R Cosimano
(74) *Attorney, Agent, or Firm*—Sughrue Mion, PLLC

(57) ABSTRACT

An analyzing system, comprising: a sample processor for processing a sample based on a designated dilution parameter; a measurement section for measuring the sample processed by the sample processor; a dilution parameter memory for storing a first dilution parameter and a second dilution parameter which is different from the first dilution parameter and can be supplied by a user of the analyzing system; and a measurement controller for controlling the sample processor and the measurement section so as to process the sample based on the first dilution parameter and obtain a measurement value by measuring the processed sample; wherein, when a comparison of the measurement value and a predetermined threshold indicates a retest, the second dilution parameter is used for the retest, is disclosed. A diagnostic processing device and computer program product thereof are also disclosed.

17 Claims, 16 Drawing Sheets

FIG. 4

Upper and lower limit DB content

| Dilution ratio | Lower limit | Upper limit |
|---|---:|---:|
| 1-fold | 1 | 200 |
| 2-fold | 2 | 400 |
| 5-fold | 5 | 1000 |
| 10-fold | 10 | 2000 |
| 20-fold | 20 | 4000 |
| 50-fold | 50 | 10000 |

FIG. 5

Subject DB content

| Subject ID | 00009501 |
|---|---|
| Specimen number | 620004890002 |
| Measurement item name | CA19-9, HCG |
| Past result value | ○Month △Day: 400 (CA19-9)<br>◇Month ◎Day: 450 (HCG) |
| Next dilution ratio | 2-fold (CA19-9), 2-fold (HCG) |

FIG. 7

Retest selection screen — 642

| date received | 2004/10/14 12:22 | | name test 1 male | |
|---|---|---|---|---|
| Reception No: | G4 1011 4004 | | | |
| Subject ID | 00009501 | | | |

658

| Retest instructions | Result | Dilution ratio | Re test | * | R | First Measurement value | | | Second | | | Next dilution ratio | Previous value | Date |
|---|---|---|---|---|---|---|---|---|---|---|---|---|---|---|
| HCG | | | | | 0 | | | | | | | | | 04/10/12 |
| PRL | 5.6 | 1 | Z | | 2 | 1000.0< | B | 5 | | | | 1 | 5.8 | 04/10/12 |
| CA15-3 | | | | | 0 | | | | | | | 10 | 1204.0 | 04/10/12 |
| CA19-9 | 853.3 | 5 | D | h | 1 | 400.0< | B | 2 | 853.3 | D | 5 | 5 | 211.0 | 04/10/12 |
| β2MG | | | | | 0 | Through | A | | | | | | 10000.0 | 04/10/12 |
| | | | | | | | | | | | | | | |
| | | | | | | | | | | | | | | |

643 → 644 → 645 → 646 → 647 → 648 → 649 → 650 (Retest pattern) → 651 (Result status) → 652 (Measurement value) → 653 → 654 → 655 → 656 → 657

Range level · Retest pattern · Dilution ratio

FIG. 10

Measurement instruction message send from diagnostic information processing apparatus to analyzer

| Specimen No. | 620004890002 |
|---|---|
| Measurement item name | CA19-9, HCG |
| Measurement dilution ratio | 2-fold (CA19-9); 2-fold (HCG) |

FIG. 11
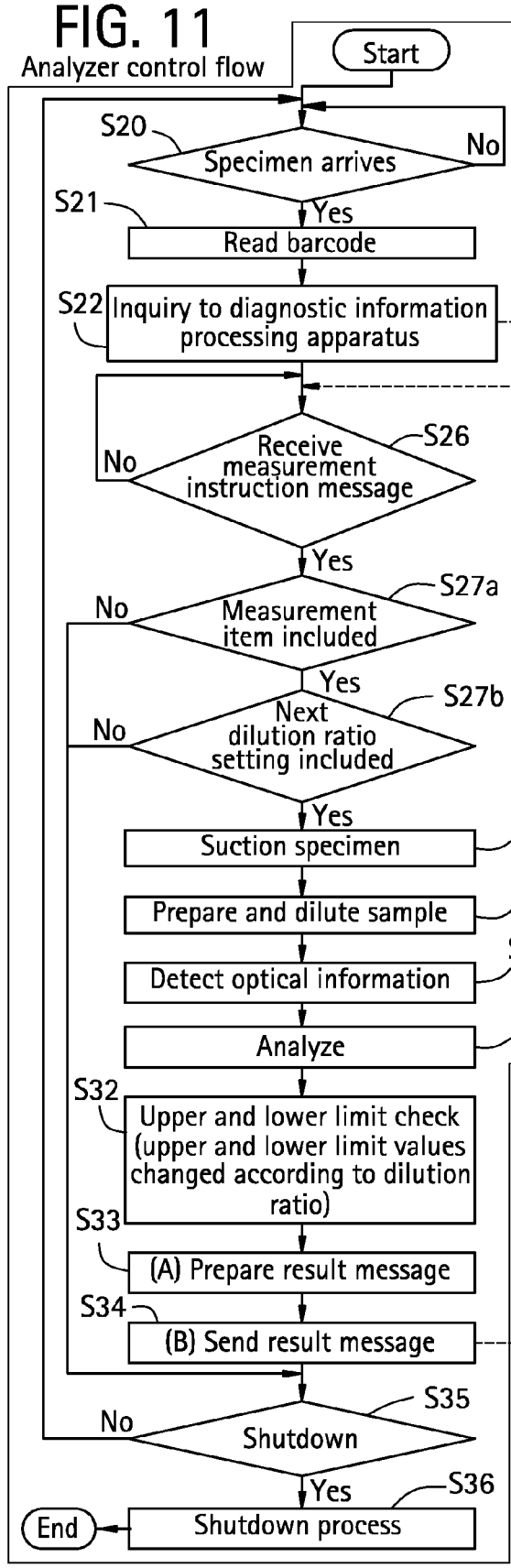
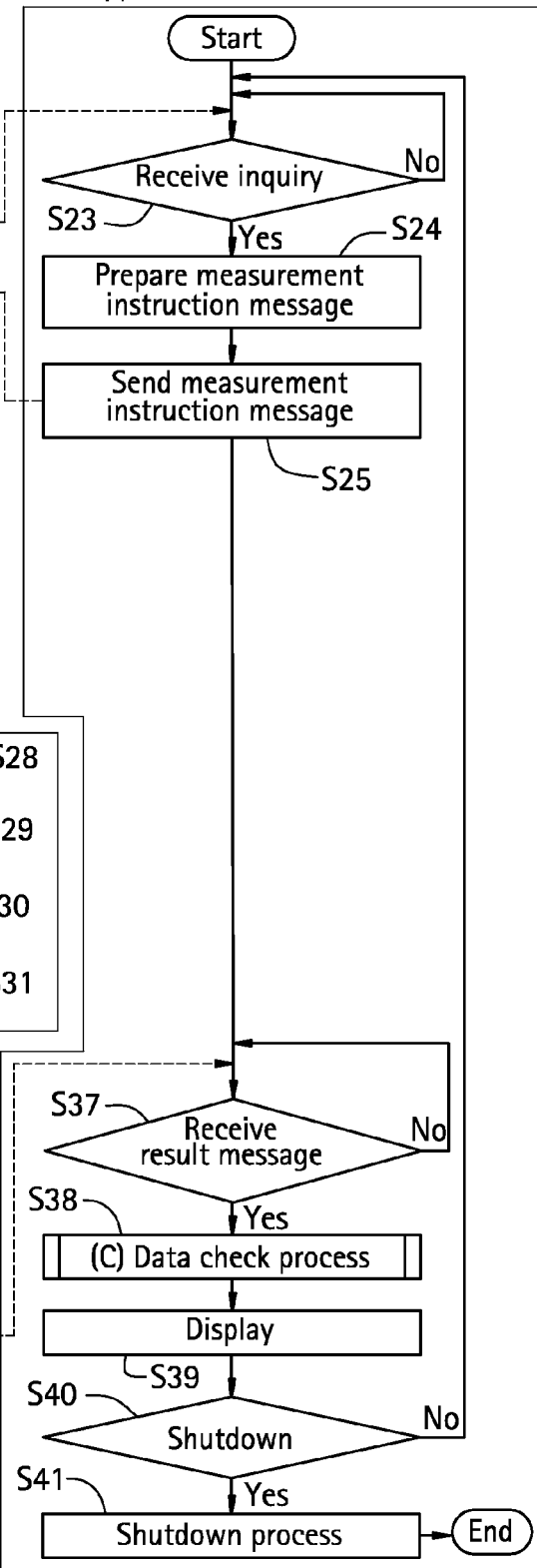

FIG. 12

Result message sent from analyzer to diagnostic information processing apparatus

| Specimen number | 620004890002 |
|---|---|
| Measurement item name | CA19-9 |
| Measurement value | 450 |
| Measurement dilution ratio | 2-fold |
| Error information | over upper limit scale anomaly |

ANALYZING SYSTEM, DIAGNOSTIC INFORMATION PROCESSING DEVICE, AND COMPUTER PROGRAM PRODUCT THEREOF

FIELD OF THE INVENTION

The present invention relates an analyzing system which comprises an analyzer for measuring a sample based on a designated dilution parameter, diagnostic information processing devices, and computer program product thereof.

BACKGROUND

Analyzers are known which are capable of diluting and measuring specimens at a plurality of dilution ratios. Inspection data processing systems provided with an auto analyzer for measuring specimens based on a dilution ratio included in analysis-request information transferred from an inspection data processing apparatus are known as diagnostic information processing systems provided with such analyzers (for example, refer to Japanese Laid-Open Patent Publication No. 4-38467).

In the inspection data processing system disclosed in Japanese Laid-Open Patent Publication No. 4-38467, the inspection data processing apparatus automatically determines a dilution ratio based on past measurement values, and includes the dilution ratio in analysis-request information which is transmitted to an auto analyzer. Then, the auto analyzer dilutes and analyzes the specimen according to the transmitted dilution ratio.

For example, this inspection processing apparatus determines a dilution ratio to transmit to an auto analyzer; a dilution ratio identical to the previous ratio is used when the previous measurement value does not exceed a maximum 80% of the measurement range, and a dilution ratio is calculated by adding "1" to the ratio of the previous measurement value, and next previous measurement value, when the previous measurement value exceeds a maximum 80% of the measurement range.

However, since the inspection data processing system disclosed in Japanese Laid-Open Patent Publication No. 4-38467 determines the dilution ratio based on past measurement values, it cannot determine which dilution ratio would be appropriate for a specimen when a specimen is to be measured for a new patient for whom there are no past measurement values and there is no optimum dilution ratio. In this instance, therefore, the measurement must be repeated a number of times by gradually increasing the dilution ratio until the specimen is diluted at an optimum dilution ratio. Thus, diagnostic efficiency is reduced when the number of measurements increases. For example, since the reagents used for measurements are extremely expensive in the case of hormone and tumor marker diagnostics, there is a need to reduce the number of measurements to as low a number as possible.

SUMMARY

The scope of the present invention is defined solely by the appended claims, and is not affected to any degree by the statements within this summary.

A first aspect of the present invention is an analyzing system, comprising: a sample processor for processing a sample based on a designated dilution parameter; a measurement section for measuring the sample processed by the sample processor; a dilution parameter memory for storing a first dilution parameter and a second dilution parameter which is different from the first dilution parameter and can be supplied by a user of the analyzing system; and a measurement controller for controlling the sample processor and the measurement section so as to process the sample based on the first dilution parameter and obtain a measurement value by measuring the processed sample; wherein, when a comparison of the measurement value and a predetermined threshold indicates a retest, the second dilution parameter is used for the retest.

A second aspect of the present invention is an analyzing system, comprising: an analyzer for measuring a sample based on a designated dilution parameter; a memory for storing a first dilution parameter which is used as a default parameter and a second dilution parameter which is different from the first dilution parameter and can be supplied by a user of the analyzing system; a retriever for retrieving one of the first dilution parameter and the second dilution parameter as a next dilution parameter from the memory based on a measurement result of the sample; and a transmitter for transmitting the retrieved next dilution parameter to the analyzer; wherein the retriever retrieves the second dilution parameter when the first dilution parameter is not suitable for measuring the sample.

A third aspect of the present invention is a diagnostic information processing device connected to an analyzer for measuring a sample based on a designated dilution parameter, comprising: a memory for storing a first dilution parameter which is used as a default parameter and a second dilution parameter which is different from the first dilution parameter and can be supplied by a user of the diagnostic information processing device; a retriever for retrieving one of the first dilution parameter and the second dilution parameter as a next dilution parameter from the memory based on a measurement result of a sample; and a transmitter for transmitting the retrieved next dilution parameter to the analyzer; wherein the retriever retrieves the second dilution parameter when the first dilution parameter is not suitable for measuring the sample.

A fourth aspect of the present invention is a computer program product for processing diagnostic information, comprising: a computer readable medium; and computer instructions, on the computer readable medium, for enabling a computer to perform the operation of: storing a first dilution parameter which is used as a default parameter and a second dilution parameter which is different from the first dilution parameter and can be supplied by a user of the computer; retrieving one of the first dilution parameter and the second dilution parameter as a next dilution parameter based on a measurement result of a sample; and transmitting the retrieved next dilution parameter to an analyzer; wherein the second dilution parameter is retrieved when the first dilution parameter is not suitable for measuring the sample.

BRIEF DESCRIPTION OF THE DRAWINGS

FIG. 4 illustrates the content of the upper and lower limit DB of the analysis apparatus of the analysis system of the embodiment shown in FIG. 1;

FIG. 5 illustrates the content of the subject DB of the diagnostic information processing apparatus of the analysis system of the embodiment shown in FIG. 1;

FIG. 7 shows a retest selection screen displayed on the display part of the diagnostic information processing apparatus of the analysis system of the embodiment shown in FIG. 1;

FIG. 10 illustrates the content of a measurement instruction message transmitted to the analyzer from the diagnostic information processing apparatus of the analysis system of the embodiment shown in FIG. 1;

FIG. 11 is a flow chart illustrating the processing performed by the diagnostic information processing apparatus and the analyzer of the analysis system of the embodiment shown in FIG. 1;

FIG. 12 illustrates the content of a result message transmitted to the diagnostic information processing apparatus from the analyzer of the analysis system of the embodiment shown in FIG. 1;

DETAILED DESCRIPTION OF THE PREFERRED EMBODIMENTS

The preferred embodiments of the present invention are described hereinafter with reference to the drawings.

The structure of an analysis system 1 of an embodiment of the present invention is described below with reference to FIGS. 1 through 8.

Figure 1:
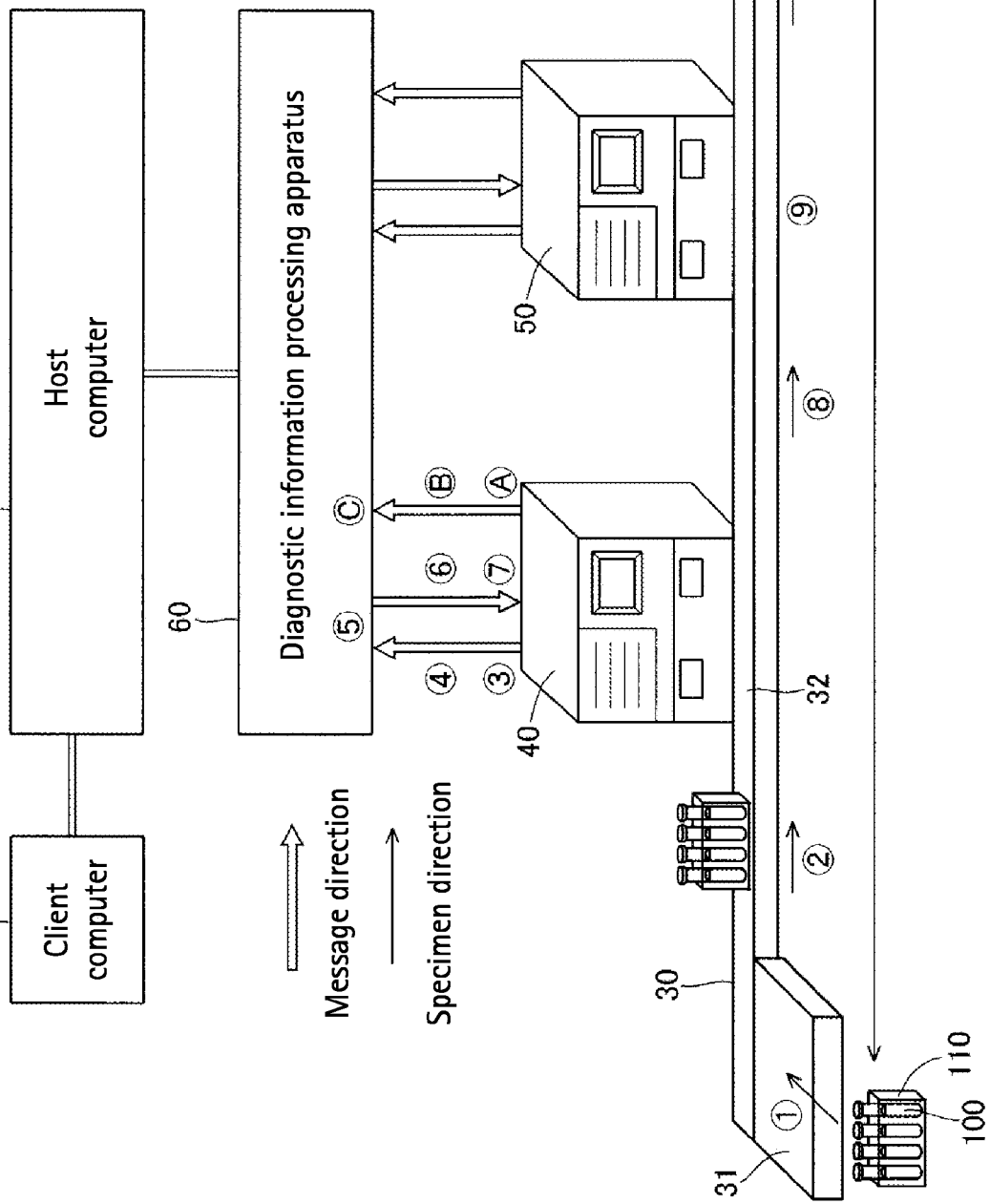
FIG. 1 briefly shows the overall structure of the analysis system of an embodiment of the present invention.
Figure 2:
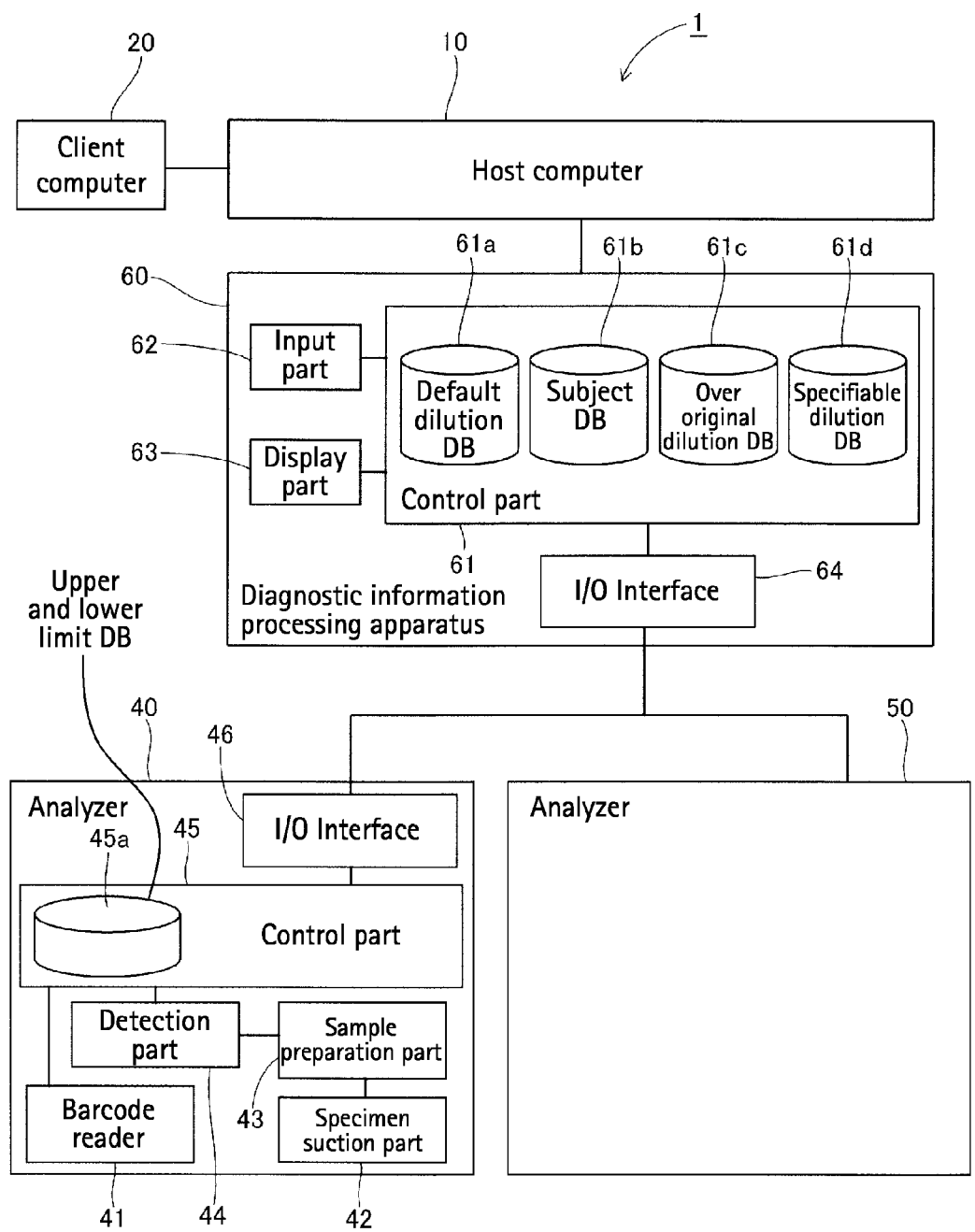
FIG. 2 is a block diagram of the analysis system of the embodiment shown in FIG. 1.
Figure 3:
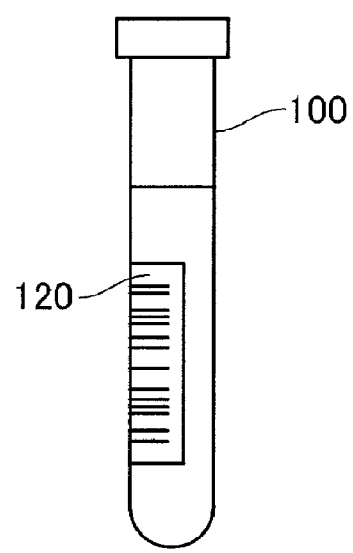
FIG. 3 is a side view of a test tube used in the analysis system of the embodiment shown in FIG. 1.

The analysis system 1 of the embodiment of the present invention performs blood examinations by processing (preparing) specimens collected from subjects at specified dilution ratios, then measuring and analyzing specific materials contained in the processed specimens. As shown in FIGS. 1 and 2, the analysis system 1 is provided with a host computer 10, client device 20, transport part 30 for transporting a rack 110 accommodating a plurality of test tubes 100, two analyzers 40 and 50, and a diagnostic information processing apparatus 60.

The host computer 10 is a computer configuring the internal system of a hospital or the like, and is connected to a client device 20 and diagnostic information processing apparatus 60 so as to be capable of wired or wireless communications. The host computer 10 has a function for issuing a barcode number (specimen number) for a barcode label 120 (refer to FIG. 3) adhered to the test tube 100 accommodated in the rack 110.

The client device 20 is disposed in the medical examination room, and is a computer for specifying requested examination items (measurement items) for a specimen collected from a subject.

The transport part 30 is configured so as to transport the rack 110 accommodating a plurality (four, in the present embodiment) of test tubes 100 (refer to FIG. 3) containing specimens collected from subjects to the analyzers 40 and 50. The transport part 30 has transport line entrance 31 for setting the rack 110 accommodating the test tubes 100 containing the unprocessed specimens, transport line 32 for transporting the rack 110 placed at the transport line entrance 31 to the analyzers 40 and 50, and a transport rack yard 33 for receiving the rack 110 accommodating the test tubes 100 containing the analyzed specimens.

The analyzers 40 and 50 are enzyme immunoassay devices arranged along the transport line 32. The analyzers 40 and 50 are respectively connected to the diagnostic information processing apparatus 60 so as to be capable of wired or wireless communication. The analyzers 40 and 50 collect the specimen in the test tube 100, process the collected specimen at a specified dilution ratio, and analyze the characteristics of the processed specimen. As shown in FIG. 2, the analyzer 40 includes barcode reader 41, specimen suction part 42, sample preparation part 43, detection part 44, control part 45, and I/O interface 46. Since the analyzer 50 has the same structure as the analyzer 40 in the present embodiment, the structure of the analyzer 40 is described below and description of the analyzer 50 is omitted.

In the present embodiment, the barcode reader 41 of the analyzer 40 is provided to read the barcode number printed on the barcode label 120 (refer to FIG. 3) adhered to the test tube 100. The specimen suction part 42 is provided to collect the specimen contained in the test tube 100 accommodated in the rack 110.

In the present embodiment, the sample preparation part 43 processes specimens to a plurality of dilution ratios, and when a specimen collected by the sample suction part 42 is processed, the specimen is diluted to a specified dilution ratio among the plurality of dilution ratios. In the present embodiment, the sample preparation part 43 is capable of changing the dilution ratio to 1-fold, 2-fold, 5-fold, 10-fold, 20-fold, and 50-fold. The sample preparation part 43 also has a function for adding various reagents to the specimen in accordance with the requested examination item (measurement item). In the description of the present embodiment, "processing a specimen at a 1-fold dilution ratio" means the specimen is not diluted.

The detection part 44 is provided to obtain optical information by measuring the specimen processed by the sample preparation part 43. The control part 45 is provided to sends and receives information to and from the diagnostic information processing apparatus 60 through the I/O interface 46, and controls the operations of the barcode reader 41, specimen suction part 42, sample preparation part 43, and detection part 44. The control part 45 is configured by a CPU, ROM, RAM, hard disk and the like. The control part 45 has the function of analyzing the characteristics of the specimen processed by the sample preparation part 43 at the specified dilution ratio and measured by the detection part 44, and obtaining measurement values. The control part 45 includes an upper limit and lower limit DB (database) 45a for storing an upper limit value representing the upper limit of the measurement value, and a lower limit value representing the lower limit of the measurement value. An upper limit value and lower limit value corresponding to a dilution ratio are stored for every measurement item in the upper limit and lower limit DB 45a.

Specifically, since the specimen dilution ratio is changeable among 1-fold, 2-fold, 5-fold, 10-fold, 20-fold, and 50-fold, a lower limit value 1 and upper limit value 200 corresponding to the dilution ratio 1-fold are be stored in the upper and lower limit DB 45*a*, as shown in FIG. 4. Similarly, the upper limit and lower limit DB 45*a* also stores a lower limit value 2 and upper limit value 400 corresponding to the dilution ratio 2-fold, lower limit value 5 and upper limit value 1000 corresponding to the dilution ratio 5-fold, lower limit value i0 and upper limit value 2000 corresponding to the dilution ration 10-fold, lower limit value 20 and upper limit value 4000 corresponding to the dilution ratio 20-fold, and lower limit value 50 and upper limit value 10,000 corresponding to the dilution ratio 50-fold. The lower limit values and upper limit values stored in the upper limit and lower limit DB 45*a* of the analyzer 40 may be minimum values and maximum values of the measurement values calculable by the control part 45 when analyzing the characteristics of a specimen, or may be the maximum value and minimum value of a measurement values obtainable with sufficient reliability given the measurement accuracy of the analyzer 40. The table shown in FIG. 4 shows the upper limit and lower limit values of CA19-9, and tables with upper and lower limit values for other measurement items, such as HCG, are also stored in the upper and lower limit DB 45*a*.

In the present embodiment, the control part 45 has the function of reading the upper limit value for comparison with the measurement value from the upper and lower limit DB 45*a* according to the dilution ratio of the specimen processed by the sample preparation part 43, and compares the read upper limit value with the measurement value. Similarly, the control part 45 has the function of reading the lower limit value for comparison with the measurement value from the upper and lower limit DB 45*a* according to the dilution ratio of the specimen processed by the sample preparation part 43, and compares the read lower limit value with the measurement value.

The diagnostic information processing apparatus 60 is connected to the host computer 10 and the two analyzers 40 and 50 so as to be capable of wired or wireless communication. The diagnostic information processing apparatus 60 is configured by a computer, and includes a control part 61, input part 62, display part 63, and I/O interface 64. The control part 61 is configured by a CPU, ROM, RAM, hard disk and the like.

The control part 61 is provided to send and receive information to/from the analyzers 40 and 50 through the I/O interface 64, and control the operations of the input part 62 and display part 63. The control part 61 has a default dilution DB 61*a* for storing the default dilution ratios, subject DB 61*b* for storing subject information, over original dilution DB 61*c*, and specifiable dilution DB 61*d* for storing the dilution ratios that can be specified for the sample preparation part 43 of the analyzer 40. The default dilution DB 61*a* stores default (original) dilution rates corresponding to the requested examination items (measurement items). Although the default dilution ratio is 1-fold in the present embodiment, it is not necessarily limited to 1-fold and may be a dilution ratio relative to a normal specimen. The default dilution ratio is set beforehand for each measurement item using the input part 62 by the data entry personnel (a person from a manufacturer) when the diagnostic information processing device 60 is installed at a hospital, laboratory center or the like. The subject DB 61*b* stores tables associating subject ID, specimen number, measurement item name, past result values, and next dilution ratio, as shown in FIG. 5. The specimen number is a barcode number (specimen number) generated by the host computer 10, and the subject ID is a number identifying the subject who provided the specimen corresponding to the specimen number. The measurement item name (CA-19-9 and HCG in the example of FIG. 5) are requested examination items (measurement items through received as input from the client device 20 and input to the host computer 10. The requested exam item (measurement item) are not only input from the client device 20, they may also be input from the diagnostic information processing apparatus 60. The past result values (CA19-9=400 and HCG=450 in the example of FIG. 5), and the date corresponding to the result value and the measurement item are stored as past result values. The result value is the analysis result of a specimen ultimately displayed on the display part 63 to report to the user of the analysis system 1. When the subject is an initial exam subject, there is no past result value information stored for the subject. A dilution ratio when performing a next measurement of a specimen collected from a subject is associated with a measurement item and stored as a next dilution ratio.

In the present embodiment, an over original dilution ratio that is larger than the default dilution ratio is stored in the over original dilution DB 61*c*. An over original dilution ratio is set for each examination item using the input part 62 by data entry personnel (a person from a manufacturer) or the user of the analysis system 1, and in the present embodiment the dilution ratio is 10-fold or more than the default dilution ratio. The over original dilution ratio is a dilution ratio specified for retesting when the measurement value at the default dilution ratio exceeds the upper limit value.

In the present embodiment, the specifiable dilution DB 61*d* stores ratios of 1-fold, 2-fold, 5-fold, 10-fold, 20-fold, and 50-fold which are processable by the sample preparation part 43.

The display part 63 is provided to display a screen for confirming the examination progress status of the analysis system 1 (progress confirmation screen), screen for confirming result values and selecting result values of a specific specimen (retest selection screen), and a maintenance screen for setting the data check method and changing the basic values for each measurement item (master setting screen).

Figure 6:
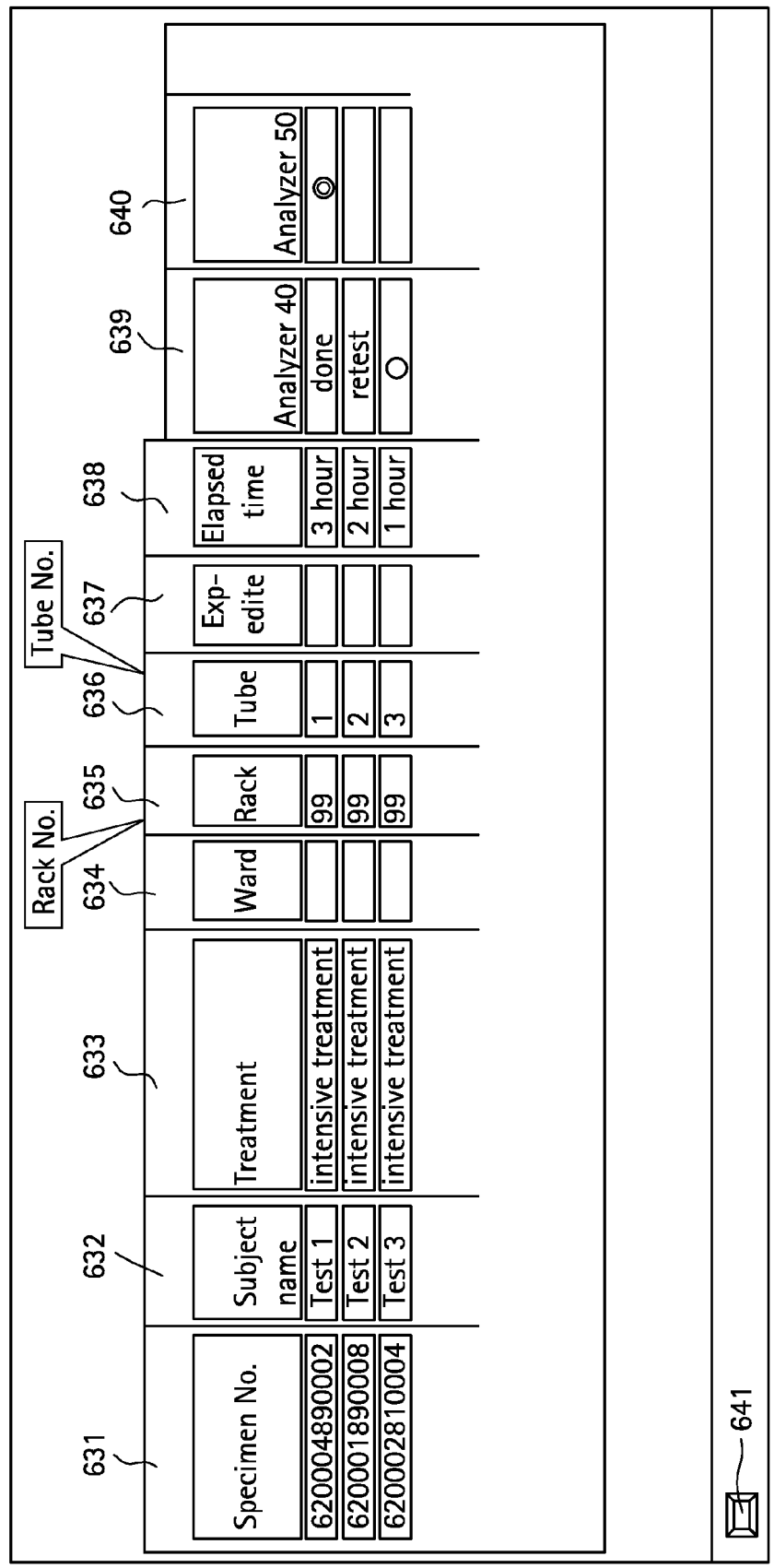
FIG. 6 shows a progress confirmation screen displayed on the display part of the diagnostic information processing apparatus of the analysis system of the embodiment shown in FIG. 1.

As shown in FIG. 6, the progress confirmation screen displays a display column 631 for displaying specimen numbers, display column 632 for displaying patient names, display column 633 for displaying examination and treatment information, display column 634 for displaying hospital wards, display column 635 for displaying the number of the rack 110 ("rack" on the screen), display column 636 for displaying the position of a test tube 100 ("tube" on the screen) in the rack 110, display column 637 for displaying specimens for expedited examination, display column 638 for displaying elapsed time, display column 639 for displaying specimen processing status in the analyzer 40, and display column 640 for displaying specimen processing status in the analyzer 50. Barcode numbers of the barcode label 120 (refer to FIG. 3) that were read by the barcode reader 41 of the analyzer 40 are displayed in the display column 631 for displaying specimen numbers, and the name of the subject who provided the specimen is displayed in the display column 632. Diagnostic and treatment information is displayed in the display column 633 for displaying treatment information, and the hospital ward in which the treatment information of the requested examination exists is displayed in the display column 634 for displaying the hospital ward. A flag (for example, "C") warning of the need for expedited examination of a specimen is displayed in the display column 637 for displaying specimens for expedited examination, so as to allow confirmation by a technician. The elapsed time from the start of reading of the barcode label 120 by the barcode reader 41 of the analyzer 40 is displayed in the display column 638 for displaying elapsed time. Displayed in the display columns 639 and 640 for displaying the specimen processing status of the analyzers 40 and 50, for respective specimens, are either "○" indicating the presence of a performed measurement item, "retest" indicating the need for retesting, "done" indicating confirmation (approval) of the result value obtained from the specimen, and "⊚" indicating result value confirmation completion for all requested examination items. A retest examination screen is displayed by clicking the button 641 located at the bottom of the progress confirmation screen.

As shown in FIG. 7, the retest selection screen displays a display column 642 for displaying various information relating to a specific specimen, display column (button) 643 for displaying requested examination items, display column 644 for displaying result values ("result" on the screen) obtained by measurements, display column 645 for displaying the dilution ratio ("dilution ratio" on the screen) at which the result value was obtained, display column 646 for displaying the reason for retesting ("retest" on the screen), display column 647 for displaying the result value level ("*" on the screen), display column 648 for displaying result restart ("R" on the screen), display columns 649 and 650 for respectively displaying first and second measurement values, display columns 651 and 652 for respectively displaying the reasons for retesting of first and second measurement values, display columns 653 and 654 for respectively displaying the dilution ratios at which first and second measurement values were obtained, display column (entry column) 655 for displaying a next dilution ratio ("next dilution ratio" on the screen), display column 656 for displaying a previous measurement value ("previous value" on the screen), display column 657 for displaying the data on which the previous measurement value was obtained, and button 658 for executing a retest command.

A plurality of requested examination items (measurement items) that the analyzer 40 can perform are displayed in the display column (button) 643. The measurement items for display in the display column (button) 643 can be measurement items for each specimen specified for examination by the client device 20. The result values ultimately obtained by a plurality of measurements, including retesting are displayed in the display column 644. Displayed in the display columns 646 and 651 are each type of error information described later, such as a flag "A" indicating the generation of a "device error", flag "B" indicating the generation of an "over upper limit scale anomaly" and "over lower limit scale anomaly", flag "C" indicating the generation of "low dilution value check anomaly", flag "G" indicating a "dispersion check anomaly", flag "D" indicating the generation of a "previous value check anomaly", and flag "Z" indicating none of the above occurred. With regard to specific measurement items, a flag "O" indicating an unperformed test or need for a retest, flag "1" indicating a need for approval of a result value obtained from a specimen, and flag "2" indicating the result value has been approved are displayed in the display column 648.

In the present embodiment, the dilution ratio (next dilution ratio) of the next measurement automatically determined based on the latest measurement value is displayed in the display column (entry column) 655. The next dilution ratio displayed in the display column (entry column) 655 can be changed using the input part 62 (refer to FIG. 2). An error message is displayed when a value is input that is at variance with the possible dilution ratios (1-fold, 2-fold, 5-fold, 10-fold, 20-fold, 50-fold) of the sample preparation part 43 of the analyzer 40.

In the retest selection screen it is possible to specify retesting of specific measurement items by clicking the display column (button) 643 in which each measurement item is displayed. When the button 658 has been clicked, it is possible to specify re-measurement of all measurement items specified for a particular specimen without clicking the display column (button) 643.

Figure 8:
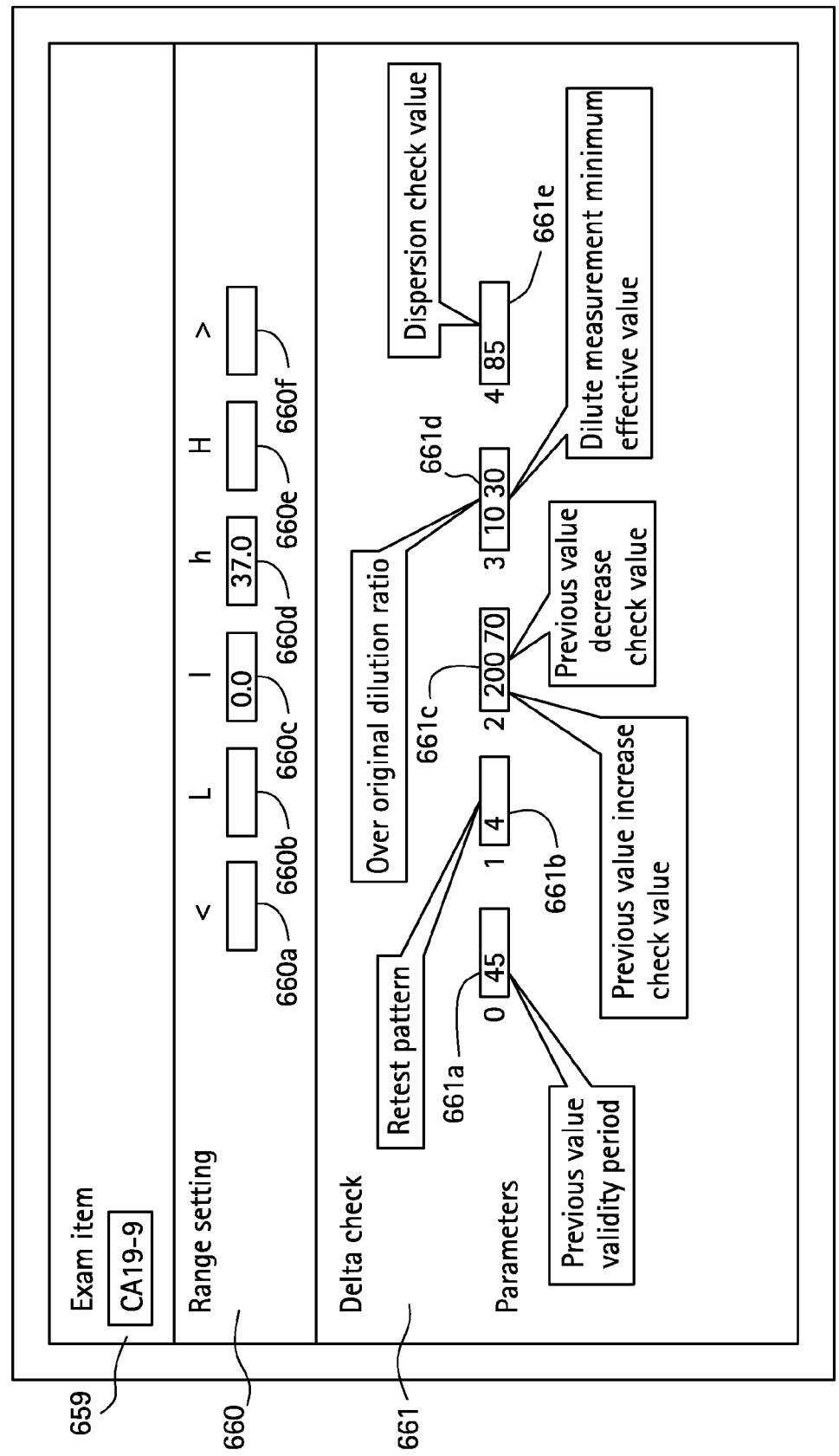
FIG. 8 shows the master setting screen displayed on the display part of the diagnostic information processing apparatus of the analysis system of the embodiment shown in FIG. 1.

The master setting screen shown in FIG. 8 is the maintenance screen, and is locked by password or the like so as to only allow a manager to change the basic values and data check method. As shown in FIG. 8, the master setting screen, displays an examination item 659 for displaying a requested examination item ("exam item" on the screen), range setting item 660 for setting the range level indicated in the display column 647 of the retest selection screen (refer to FIG. 7), and a delta check item 661 having entry columns 661a through 661e for setting a plurality of parameters for performing a data check of the measurement values.

Specifically, one ("CA-19-9" in the present embodiment) among the requested examination items is displayed in the examination item 659, as shown in FIG. 8. Entry columns 660a through 660f for dividing the range of the result values are provided in the range setting item 660, and "0.0" is entered in the entry column 660c ("l" on the screen), "37.0" is entered in the entry column 660d ("h" on the screen). Thus, when the result value of the measurement item "CA19-9" obtained by the analyzer 40 is greater than "0.0" and less than "37.0", the flag "1" is displayed in the display column 647 of the retest selection screen (refer to FIG. 7). When the result value is greater than "37.0", the flag "h" is displayed in the display column 647. The valid period of the previous value ("45" in the present embodiment) is specified beforehand in the entry column 661a ("0" on the screen) of the delta check item 661, and result values older than this set number of days become invalid. A retest pattern ("4" in the present embodiment) is specified beforehand in the entry column 661b ("1" on the screen), to specify the application of retesting. For example, the application of retesting is specified by the entry column 661b since there are measurement items that are applied without dilution even during retesting depending on the measurement item.

A previous value increase check value ("200" in the present embodiment) and a previous value decrease check value ("70" in the present embodiment) are specified in the entry column 661c ("2" on the screen). The previous value increase check value and previous value decrease check value are parameters used for suppressing specimen error (taking the wrong specimen and the like). An over original dilution ratio ("10" in the present embodiment) and dilution measurement minimum effective value ("30" in the present embodiment) are specified in the entry column 661d ("3" on the screen). When the measurement value of a specimen measured at the original dilution (default dilution ratio) is greater than the upper limit value stored in the upper limit DB 45a, the over original dilution ratio is set in the sample preparation part 43 of the analyzer 40 as the next dilution ratio, and is stored in the over original dilution DB 61c. The dilution measurement value minimum effective value is a parameter for determining whether or not the measurement value obtained by the analyzer 40 has been measured at a dilution ratio of high reliability. That is, the dilution measurement value minimum effective value is a parameter used to measure a specimen that has a possibility of being within the upper and lower limit value range at a dilution ratio that is less than the previous dilution ratio (1 level lower) in the next measurement cycle even when measured at a dilution ratio that is lower than the previous dilution ratio. A dispersion check value is specified in the entry column 661*e* ("4" on the screen). The dispersion check value (85% in the present embodiment) is a parameter for determining when the measurement value obtained in a re-measurement is suddenly a greater value compared to the measured value of a first measurement.

The sequence of the specimen examination of the analysis system 1 of the present embodiment of the invention is described below with reference to FIGS. 1 through 3, and FIGS. 9 and 10. The numbers shown in FIG. 9 correspond to the numbers in FIG. 1.

Figure 9:
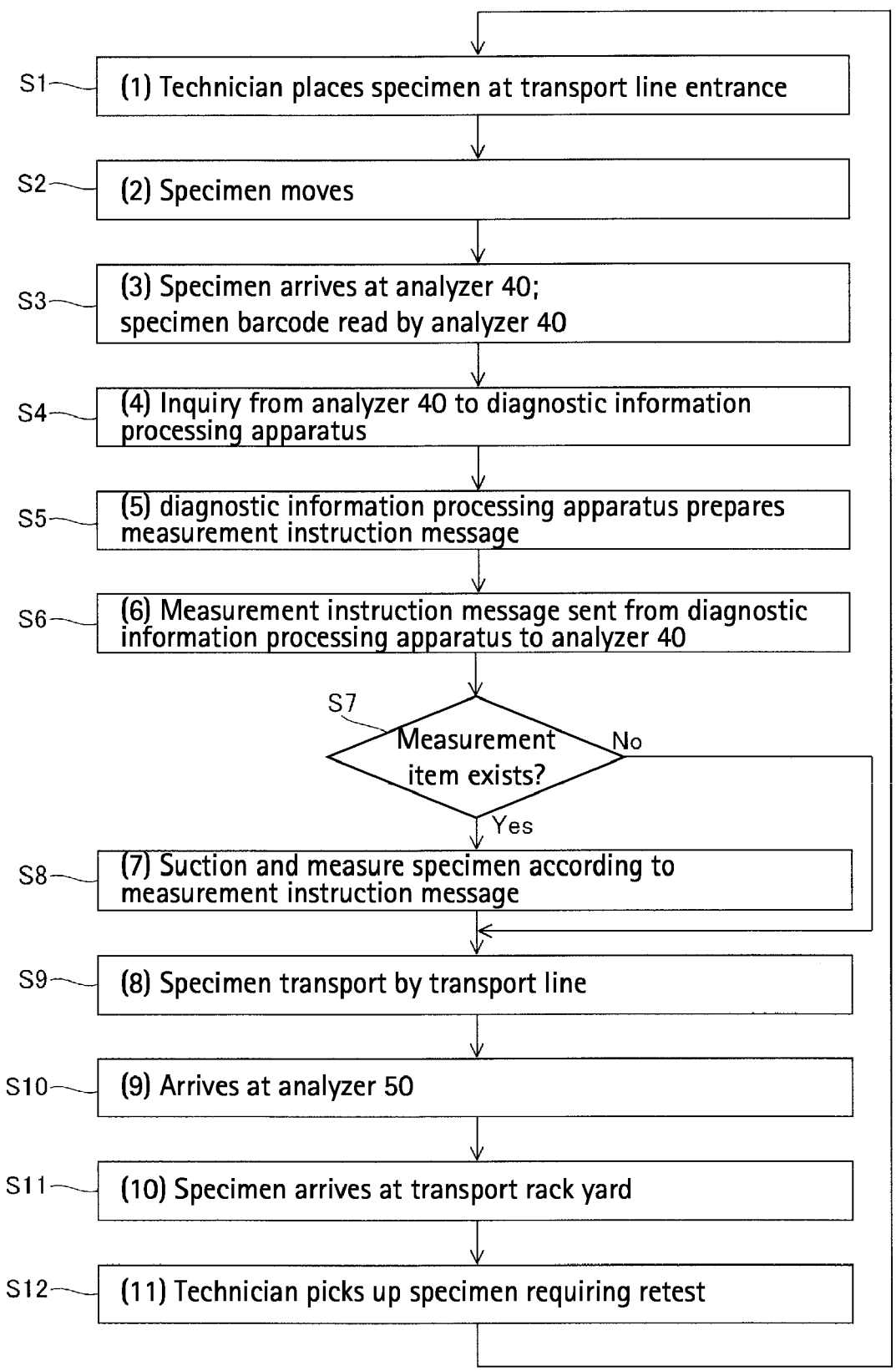
FIG. 9 is a flow chart briefly showing the operation of the specimen examination of the analysis system of the embodiment shown in FIG. 1.

A technician places the rack 110 holding the test tubes 100 at the transport line entrance 31 of the analysis system 1 shown in FIG. 1 in step S1 of FIG. 9, and thereafter the rack 110 is moved by the transport line 32 in step S2. Thus, in step S3, the rack 110 arrives at the analyzer 40, and the barcode number of the barcode label (refer to FIG. 3) adhered to the test tube 100 is read by the barcode reader 41 of the analyzer 40. Then, in step S4, requests are made from the analyzer 40 to the diagnostic information processing apparatus 60 based on the read barcode number. Specifically, the barcode number (specimen number) is sent from the analyzer 40 to the diagnostic information processing apparatus 60 to inquire about patient information and the content of measurement items (requested exam items) for the specimen corresponding to the barcode. Then, in step S5 of the present embodiment, the control part 61 of the diagnostic information processing apparatus 60 acquires the measurement items and the dilution ratio (next dilution ratio) corresponding to the measurement items from the subject DB 61*b* based on the barcode received from the analyzer 40, and prepares a measurement instruction message. Thereafter, in step S6, the control part 61 of the diagnostic information processing apparatus 60 sends the measurement instruction message prepared in step S5 to the analyzer 40. The measurement instruction message includes information of the specimen number read by the barcode reader 41, measurement items names to be performed on the specimen corresponding to this specimen number, and measurement dilution ratios for these measurement items.

Then, in step S7, a determination is made by the analyzer 40 as to whether or not there are measurement items included in the measurement instruction message shown in FIG. 10. When it is determined that there are measurement items in step S7, then in step S8 the specimen contained in the test tube 100 is suctioned for measurement by the specimen suction part 42 (refer to FIG. 2) of the analyzer 40 according to the measurement instruction message. After the specimen has been suctioned, the rack 110 is moved in the direction of the analyzer 50 by transporting the rack 110 via the transport line 32 in step S9. When it is determined there are not measurement items in step S7, however, the routine advances to step S9 without performing the measurement in step S8, and the above process is executed. Thus, in step S10 the rack 110 arrives at the analyzer 50 and the processes from steps S3 to S9 are executed, and the rack 110 is transported again by the transport line 32. In step S11, the rack 110 transported by the transport line 32 arrives at the transport rack yard 33, and thereafter in step S12, the specimen needed for retesting is picked up by the technician and returned to step S1.

The control flow executed by the diagnostic information processing apparatus 60 and analyzer 40 of the analysis system 1 of the present invention for the execution of the above sequence is described below with reference to FIGS. 2 through 4, and FIGS. 10 through 12. The alphabetical references in FIG. 11 correspond to the alphabetical references in FIG. 1.

On the analyzer 40 side, first, in step S20 of FIG. 11, a determination is made as to whether or not the rack 110 holding the test tube 100 containing the specimen has arrived at the analyzer 40, and when it is determined that the rack 110 has arrived, then, in step S21, the barcode number of the barcode label 120 (refer to FIG. 3) adhered to the test tube 100 is read by the barcode reader 41. When it is determined in step S20 that the rack 110 has not arrived at the analyzer 40, the determination of step S20 is repeated until the rack 110 has arrived at the analyzer 40. Then, in step S22, a request is made from the analyzer 40 to the diagnostic information processing apparatus 60 (sending of barcode number).

On the diagnostic information processing apparatus 60 side, in step S23, the a determination is made as to whether or not a request (barcode) has been received from the analyzer 40. When it is determined in step S23 that a request has not been received, the determination of step S23 is repeated until a request is received. On the other hand, when it is determined in step S23 that a request has been received, then in step S24 the control part 61 of the diagnostic information processing apparatus 60 prepares the measurement instruction message shown in FIG. 10 by reading the measurement item names and next dilution ratio from the subject DB 61*b* based on the received barcode number. The prepared measurement instruction message is sent from the diagnostic information processing apparatus 60 to the analyzer 40 in step S25.

On the analyzer 40 side, in step S26, a determination is made as to whether or not the measurement instruction message (refer to FIG., 10) sent by the diagnostic information processing apparatus 60 in step S25 has been received. When it is determined that the measurement instruction message has not been received in step S26, the determination of step S26 is repeated until the measurement instruction message is received. When it is determined that the measurement instruction message has been received in step S26, then a determination is made as to whether or not the measurement instruction message contains measurement items in step S27*a*. When it is determined that there are measurement items in step S27*a*, then in step S27*b* a determination is made as to whether or not the measurement instruction message contains a next dilution ratio. When it is determined that the measurement instruction message contains a next dilution ratio in step S27*b*, then in step S28 the specimen in the test tube 100 is suctioned (collected) by the specimen suctioning part 42 (refer to FIG. 2) of the analyzer 40. In step S29, a sample is prepared (the specimen is processed) at the specified dilution ratio for each measurement item by the sample preparation part 43 (refer to FIG. 2) of the analyzer 40. That is, in the present embodiment, the specimen is processed at the specified measurement dilution ratio by the sample preparation part 43 of the analyzer 40 via the measurement instruction message that includes the measurement dilution ratio prepared by the control part 61 of the diagnostic information processing apparatus 60. Thereafter, instep S30, the detection part 44 (refer to FIG. 2) detects optical information from the sample (specimen) by illuminating the sample obtained in the process of step S29 with light, then in step S31, the detected optical information is analyzed and the measurement values are obtained by the control part 45 (refer to FIG. 2) of the analyzer 40.

In step S32 of the present embodiment, the control part 45 (refer to FIG. 2) of the analyzer 40 executes the upper limit and lower limit value check on the measurement value obtained by analyzing the optical information in step S31.

Specifically, the control part 45 references the lower limit and upper limit values corresponding to the dilution ratio included in the measurement instruction message (refer to FIG. 10) received in step S26 using the upper limit and lower limit DB 45a (refer to FIG. 4), and determines whether the measurement value obtained from the measurement sample is between the lower limit and upper limit values. For example, in the case of the dilution ratio of "2-fold" shown in FIG. 2 corresponding to the measurement item "CA19-9" of the measurement instruction message, the control part 45 references the lower limit 2 and upper limit 400 corresponding to 2-fold in the upper and lower limit DB 45a shown in FIG. 4. Then, the control part 45 of the analyzer 40 determines whether or not the measurement value obtained from the specimen is between the lower limit value 2 and the upper limit value 400.

In step S33, a result message, such as shown in FIG. 12, is prepared based on the measurement result obtained by the control part 45 of the analyzer 40. When there are a plurality of measurement items in the measurement instruction message (refer to FIG. 10) received in step S26, a plurality of result messages are prepared for the measurement items. The result message includes information such as specimen number, measurement item name, measurement value, measurement dilution ratio, and error information, as shown in FIG. 12. In the present embodiment, since the measurement value (450) of the measurement item (CA19-9) at 2-fold dilution is greater than the upper limit value (400) of the upper and lower limit DB 45a corresponding to a 2-fold dilution ratio, error information "over upper limit scale anomaly" is generated.

The analyzer 40 sends the result message (refer to FIG. 12) prepared in step S33 to the diagnostic information processing apparatus 60 in step S34. Thereafter, in step S35, the analyzer 40 determines whether or not to shutdown. When it has been determined in step S27a that there are no measurement items in the measurement instruction message, and when it has been determined in step S27b that there is no next dilution ratio in the measurement instruction message, the routine advances to step S35 and the analyzer 40 determines whether or not to shutdown. When a shutdown determination has been made in step S35, the shutdown process is executed by the analyzer 40 in step S36, and the processes of the analyzer 40 end. The series of processes in steps S20 through S22 and steps S26 through S34 of the analyzer 40 are repeated until the analyzer 40 makes a shutdown determination.

On the other hand, a determination as to whether or not a result message has been received is made in step S37 on the diagnostic information processing apparatus 60 side when a result message (refer to FIG. 12) has been received from the analyzer 40 in step S34. When a result message has not been received, then the determination of step S37 is repeated until a result message is received. When it is determined in step S37 that a result message has been received, then in step S38 the data check process is performed based on the information included in the result message. The result value and measurement value are displayed on the display part 63 (refer to FIGS. 2, 6, and 7) of the diagnostic information processing apparatus 60 in step S39 based on the result of the predetermined data check process performed in step S38. Thereafter, the diagnostic information processing apparatus 60 determines whether or not to shutdown in step S40. When a shutdown determination has been made in step S40, the shutdown process is executed by the diagnostic information processing apparatus 60 in step S41, and the processes of the diagnostic information processing apparatus 60 ends. The series of processes in steps S23 through S25 and steps S37 through S39 of the diagnostic information processing apparatus 60 are repeated until a shutdown is determined by the diagnostic information processing apparatus 60 in step S40.

Details of the data check process in step S38 are described below with reference to FIGS. 1, 2, 4, 5, 7, 8, and FIGS. 12 through 15.

When a result message (refer to FIG. 12) is received from the analyzer 40, a determination is made in step S51 (refer to FIG. 13) whether or not an error has occurred in the analyzer 40. Specifically, it is determined whether or not the information "device error" is included in the error information of the analyzer 40. The "device error" is mainly caused by an anomaly (tube blockage, empty reagent and the like) of the analyzer 40. When it is determined in step S51 that a device error has occurred, then in step S52 the measurement dilution ratio included in the result message is immediately set as the next dilution ratio of the subject DB 61b. In this case, the flag "A" indicating the generation of "device error" is displayed at predetermined positions of the display columns 646, 651, and 652 of the retest selection screen shown in FIG. 7. Thereafter, the routine continues to step S53 shown in FIG. 15, a determination is made as to whether or not the current measurement is an initial measurement (first measurement on this day). When the current measurement is determined to be an initial measurement in step S53, a required retesting condition is set for the item in step S54. When the item required retesting condition is set in step S54, "0" is displayed in the display column 648 to display the result status of the retest selection screen shown in FIG. 7, and retesting is executed. When the current measurement is determined to not be an initial measurement in step S53, a required confirmation condition is set for the item in step S55. When the item required confirmation condition is set in step S55, "1" is displayed in the display column 648 of the retest selection screen shown in FIG. 7, and technician confirmation is required.

When it has been determined that a device error has not occurred in step S51, a determination is made in step S56 as to whether or not the measurement value is an over the upper limit scale anomaly. Specifically, it is determined whether or not the information "over upper limit scale anomaly" is included in the error information of the result message. The "over upper limit scale anomaly" information indicates that the measurement value exceeds the predetermined upper limit value stored in the upper limit Db 45a, as previously described. This error information indicates that the dilution ratio used in the measurement of the specimen is unsuitable and a retest is required. When an over upper limit scale anomaly is determined in step S56, then the measurement value is changed to "upper limit<" and displayed on the retest selection screen (refer to FIG. 7) in step S57. With regard to the measurement item "CA15-3" on the retest selection screen shown in FIG. 7, for example, when the measurement value at a 5-fold dilution ratio is determined to be over the upper limit scale anomaly by the analyzer 40, the measurement value is changed to "1000.0<" and displayed in the display column 649 based on the upper limit value of 1000 of the upper and lower limit DB 45a corresponding to the 5-fold dilution ratio. In this case, the flag "B" indicating the generation of "over upper limit scale anomaly" is displayed at predetermined positions of the display columns 646, 651, and 652 of the retest selection screen shown in FIG. 7. Thereafter, in step S58, a determination is made as to whether or not the current measurement dilution ratio is the original (default dilution ratio). When the current measurement dilution ratio is not the original ratio in the determination of step S58, then in step S59 a determination is made as to whether or not the current measurement dilution ratio is a maximum effective value. The maximum effective value is the maximum dilution ratio of the sample preparation part 43 of the analyzer 40, and in the present embodiment the maximum value is set at 50-fold (refer to FIG. 4).

When the current measurement dilution ratio is determined to be the maximum effective value (50-fold) in step S59 of the present embodiment, then a blank entry is set in the next dilution ratio column of the subject DB 61*b* in step S60. That is, when the measurement value obtained at the maximum effective dilution ratio is greater than the upper limit value in the upper limit and lower limit DB 45*a* via the processes of steps S56 and S59, nothing is stored in the next dilution ratio of the subject DB 61*b*. Thus, since the determination result is "NO" in step S27*b* (refer to FIG. 11) in the next measurement, the specimen of the subject from whom the specimen was collected is not measured by the analyzers 40 and 50, and "Through" is displayed in the display column 649 of the retest selection screen shown in FIG. 7.

Since measurement is impossible in the analysis system 1 when the measurement value obtained at a maximum effective dilution ratio is greater than the upper limit value of the upper and lower limit DB 45*a*, the user analyzes the specimen of the subject who provided the specimen microscopically, or manually dilutes the specimen at a ratio greater than 50-fold and measures the specimen using the analyzer 40.

When the current measurement dilution ratio is determined to be the original ratio in step S58 of the present embodiment, the value "over original dilution ratio" stored in the over original dilution ratio DB 61*c* is set in the next dilution ratio of the subject DB 61*b* (see step S61). That is, in the present embodiment, if the measurement value obtained with the specimen at the default dilution ratio (original ratio) is greater than the upper limit value of the upper and lower limit DB 45*a*, the over original dilution ratio is stored in the next dilution ratio of the subject DB 61*b* via the processes of steps S56 and S58. In this case, over original dilution ratio is displayed in the display column (entry column) 655 on the retest selection screen (refer to FIG. 7). The dilution ratios displayed in the display column (entry column) 655 including the over original dilution ratio are changeable via the input part 62 (refer to FIG. 2), and the changed over original dilution ratio is set in the next dilution ratio of the subject DB 61*b*.

When it is determined that the current measurement dilution ratio is not the maximum effective value (50-fold) in step S59 of the present embodiment, the dilution ratio one level higher than the current measurement dilution ratio is read from the specifiable dilution ratio DB 61*d* and set in the next dilution ratio of the subject DB 61*b* (see step S62). That is, in the present embodiment, if the measurement value obtained with the specimen at a dilution ratio greater than the default dilution ratio (original ratio) is greater than the upper limit value of the upper and lower limit DB 45*a*, the dilution ratio one level higher is stored in the next dilution ratio of the subject DB 61*b* via the processes of steps S56 and S58. For example, when a specimen is measured at a 2-fold measurement dilution ratio, the 5-fold dilution ratio, which is one level higher than 2-fold, is set in the next dilution ratio of the subject DB 61*b*. After the processes of steps S60 through S62 have been executed, the routine moves to step S52, and steps S53 through S55 are performed.

On the other hand, when the measurement value obtained by the analyzer 40 is determined to not be an over the upper limit scale anomaly in step S56, a determination is made in step S63 as to whether or not the measurement value is an over the lower limit scale anomaly. Specifically, it is determined whether or not the information "over lower limit scale anomaly" is included in the error information of the result message (refer to FIG. 12). The "over lower limit scale anomaly" indicates that the measurement value is less than a predetermined lower limit value stored in the upper limit DB 45*a*. When an over lower limit scale anomaly is determined in step S63, then the measurement value is changed to "lower limit>" and displayed on the retest selection screen in step S64. In this case, a flag "B" indicating the occurrence of an "over lower limit scale anomaly" is displayed at a predetermined position in the display columns 646, 651, and 652 of the retest selection screen. Thereafter, a determination is made in step S65 as to whether or not the current measurement dilution ratio is an original ratio. When the current measurement dilution ratio is not the original ratio in the determination of step S65, then in step S66 the dilution ratio one level lower than the current measurement dilution ratio is read from the specifiable dilution ratio DB 61*d* and set in the next dilution ratio of the subject DB 61*b*.

That is, when the measurement value of a specimen at a predetermined dilution ratio is less than the lower limit value of the upper and lower limit DB 45*a*, the dilution ratio one level lower than a predetermined dilution ratio is stored in the next dilution ratio of the subject DB 61*b*, via the processes of steps S63 and S65, such that this next dilution ratio is specified to the sample preparation part 43 by the control part 61 of the diagnostic information processing apparatus 60 at the next dilution time. After the process of step S66 has been executed, the routine moves to step S53, and steps S53 through S55 are performed.

When the measurement value is determined to not be an over the lower limit scale anomaly in step S63, a determination is made in step S67 as to whether or not the current dilution ratio is an original ratio. When the current measurement dilution ratio is not the original ratio in the determination of step S67, then in step S68 a determination is made as to whether or not it is a dilution low value check anomaly. Specifically, a dilution low value check anomaly is determined when a value obtained by dividing the measurement value by the current dilution ratio is less-than the "minimum effective value for dilute measurement (30 in the present embodiment)" settable in the entry column 661*d* of the delta check item 661 on the master setting screen (refer to FIG. 8). For example, when the "minimum effective value for dilute measurement" is 30, that is, when the dilution ratio is 10-fold and the measurement value is less than 300, as shown in FIG. 8, a dilution low value check anomaly is determined since the value obtaining by dividing the measurement value by the current dilution ratio is less than 30. Thus, it is possible to determine whether or not a measurement value is within a sufficient measurement range even when the dilution ratio is one level lower than the current measurement dilution ratio, that is, whether or not a specimen measured at the current measurement dilution ratio is "over diluted". Therefore, it is possible to obtain a highly reliable measurement value since it is possible to obtain a measurement value from a specimen that has not been unnecessarily diluted. In the case of a dilution low value check anomaly, a flag "C" indicating the occurrence of a "dilution low value check anomaly" is displayed at predetermined locations in the display columns 646, 651, and 652 of the retest selection screen. When the current measurement has been determined to be a dilution low value check anomaly in step S68, then in step S69 the dilution ratio one level lower than the current measurement dilution ratio is read from the specifiable dilution ratio DB 61*d* and set in the next dilution ratio of the subject DB 61*b*. After the process of step S69 has been executed, the routine moves to step S53 of FIG. 15, and steps S53 through S55 are performed.

Figure 14:
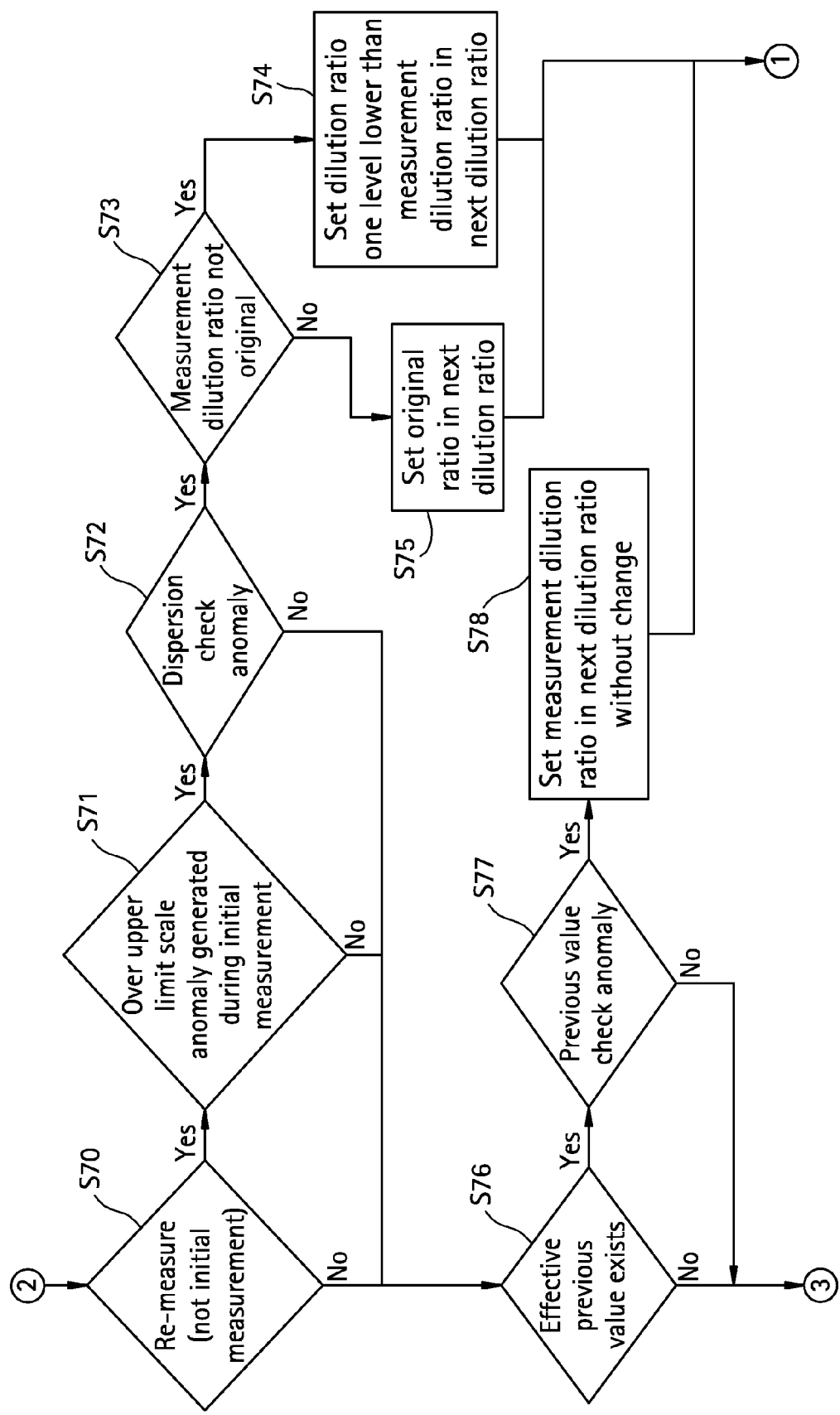
FIG. 14 is a flow chart showing details (subroutines) of the data check process performed by the diagnostic information processing apparatus of the embodiment of the analysis system shown in step S37 of FIG. 11.

When the current measurement dilution ratio is determined to be an original ratio in steps S65 and S67, a determination is made in step S70 shown in FIG. 14 as to whether or not the current measurement is a subsequent measurement (not the initial test (first measurement of the current day)). Even when the current measurement has been determined to not be a dilution low value check anomaly in step S68, the routine advances to step S70 and the above determination is made. When the current measurement has been determined to be a subsequent measurement in step S70, a determination is made in step S71 as to whether or not an over upper limit scale anomaly has occurred during the initial (first) measurement of the current day. When it has been determined that an over upper limit scale anomaly has occurred during the initial measurement in step S71, a determination is made in step S72 as to whether or not a dispersion check anomaly has occurred. Specifically, a dispersion check anomaly is determined when the current measurement value is less than a value obtained by multiplying the initial (first of the current day) measurement value by the settable"dispersion check value (85% (0.85) in the present embodiment)" in the entry column 661e of the delta check item 661 of the master setting screen (refer to FIG. 8). For example, when the "dispersion check value" is 85% as shown in FIG. 8, a dispersion check anomaly is determined if the current measurement value is less than 850 and the initial measurement value is "1000<". The dispersion check value is preferably set near 100%, such as 85% and the like. In this case, a flag "G" indicating the occurrence of a "dispersion check anomaly" is displayed at a predetermined location of the display columns 646, 651, and 652 of the retest selection screen (refer to FIG. 7).

When the current measurement value has been determined to be a dispersion check anomaly in step S72, a determination is made in step S73 as to whether or not the current measurement dilution ratio is an original ratio. When the current measurement value has been determined to not be a dispersion check anomaly in step S72, the routine advances to step S76. When the current measurement dilution ratio is not the original ratio in the determination of step S73, then in step S74 the dilution ratio one level lower than the current measurement dilution ratio is read from the specifiable dilution DB 61d and set in the next dilution ratio of the subject DB 61b. When the current measurement dilution ratio is the original ratio in the determination of step S73, then in step S75 the original ratio is read from the default dilution DB 61a and set in the next dilution ratio of the subject DB 61b. After the processes of steps S74 and S75 have been executed, the routine moves to step S53 of FIG. 15, and steps S53 through S55 are performed.

When the current measurement is determined to not be a subsequent measurement (that is, when it is an initial measurement) in step S70, a determination is made in step S76 as to whether or not the there is an valid current value. Specifically, whether or not the existing result value is within the settable "previous value valid period (45 days in the present embodiment)" in the entry column 661a of the delta check item 661 of the master setting screen (refer to FIG. 8) is determined by reference to the column of past results of the subject DB 61b. For example, when the "current valid period" is 45 days as shown in FIG. 8, a result value is deemed invalid if the previous result value is older than 45 days, and the current result value is deemed valid if obtained within the last 45 days. When it has been determined that an over upper limit scale anomaly has not occurred during the initial measurement in step S71, the routine advances to step S76 and the above determination is performed even when there is no dispersion check anomaly.

When the previous effective value has been determined to exist in step S76, a determination is made in step S77 as to whether or not there is a previous value check anomaly. The previous value check is a process for detecting a wrong specimen by comparing the result values of a current measurement and previous (most recent) measurement using examination result having little change and excluding special circumstances. Specifically, a previous value check anomaly is determined when a current measurement value satisfies either of equations (1) or (2) below.

$$(\text{current measurement value}) > (\text{previous result value}) \times \{1 + (\text{"previous increase check value"}/100)\} \quad (1)$$

$$(\text{current measurement value}) < (\text{previous result value}) \times \{1 - (\text{"previous decrease check value"}/100)\} \quad (2)$$

The "previous increase check value" and "previous decrease check value" are settable in the entry column 661c of the delta check item 661 of the master setting screen (refer to FIG. 8). For example, a previous value check anomaly is determined by equation (1) or equation (2) when the "previous increase check value" is 200 and the "previous decrease check value" is 70 and the previous measurement value is 1000, as shown in FIG. 8, and the current measurement value is greater than 3000 or less than 300. In this case, the flag "D" indicating the generation of a "previous value check anomaly" is displayed at predetermined positions of the display columns 646, 651, and 652 of the retest selection screen. When a previous value check anomaly has been determined in step S77, then in step S78 the previous measurement dilution ratio is set directly in the next dilution ratio of the subject DB 61b. After the processes of step S78 has been executed, the routine moves to step S53 of FIG. 15, and steps S53 through S55 are performed.

Figure 15:
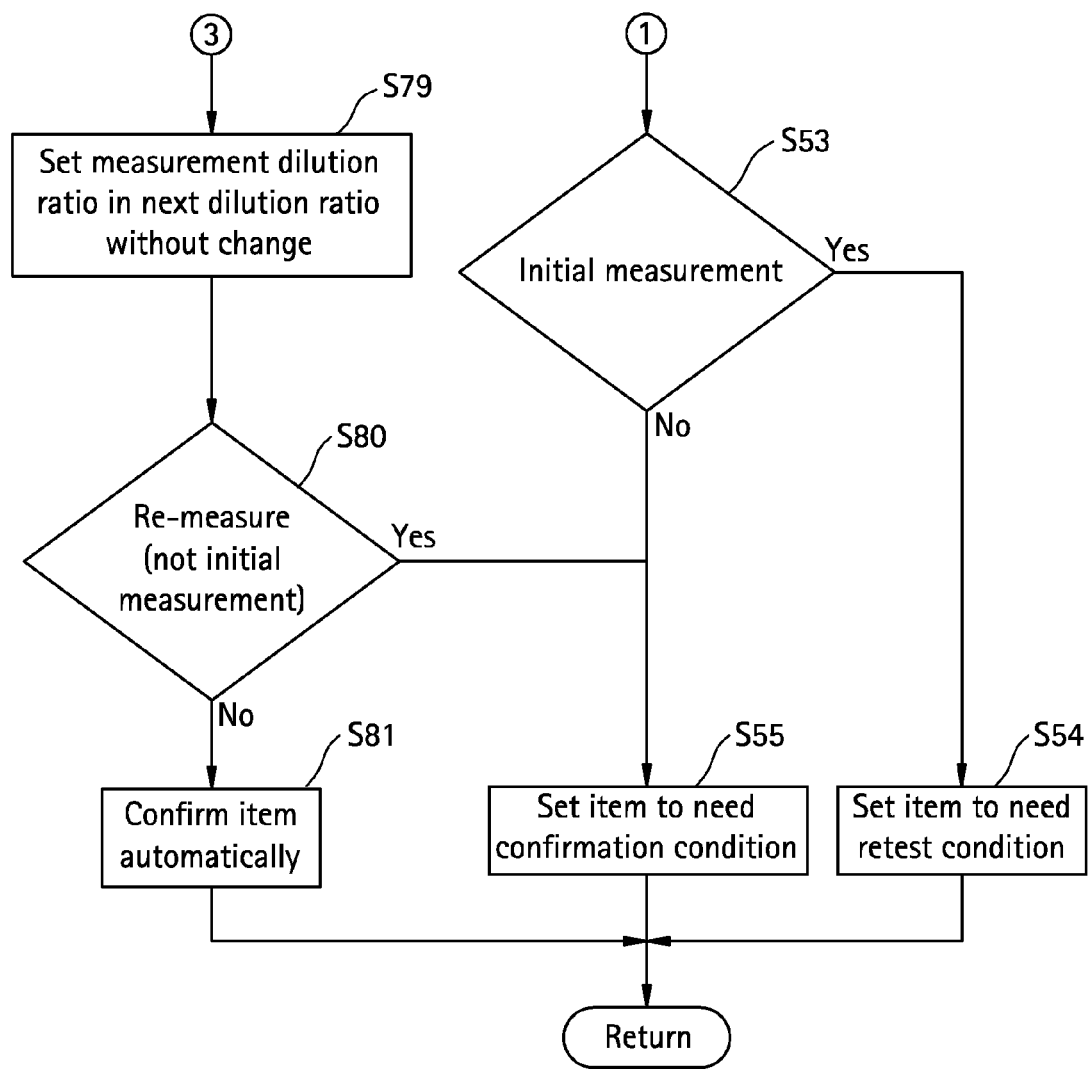
FIG. 15 is a flow chart showing details (subroutines) of the data check process performed by the diagnostic information processing apparatus of the embodiment of the analysis system shown in step S37 of FIG. 11.

When it has been determined that an effective previous value does not exist in step S76, the routine advances to step S79 of FIG. 15, and the current measurement dilution ratio is set directly in the next dilution ratio of the subject DB 61b. Even when there is no previous value check anomaly in step S77, the routine advances to step S79 and the above process is executed. Thereafter, it is determined whether or not the current measurement value is a subsequent measurement (not an initial measurement). When the current measurement has been determined to be a subsequent measurement in step S80, the item is set so as to require confirmation in step S55. When the current measurement has been determined to not be a subsequent measurement in step S80, the item is automatically confirmed in step S81. Specifically, when an item is automatically confirmed in step S81, "2" is displayed in the display column 648 for displaying the result status on the retest selection screen of FIG. 7, and the measurement value is displayed in the display column 644. In this case, the flag "Z" is displayed at predetermined positions of the display columns 646, 651, and 652 of the retest selection screen. Then, this measurement value is stored in the past result values of the subject DB 61b (refer to FIG. 5).

The measurement values that do not correspond to any among the over upper limit scale (step S56), over lower limit scale (step S63), dilution low value check anomaly (step S68), dispersion check anomaly (step S72), or previous value check anomaly (step S77) are used as result values and displayed in the display column 644 of the retest selection screen.

Since the next dilution ratio set in step S38 (refer to FIG. 11) is changeably displayed in the display column 655, the user of the analysis system 1 can pick up the specimen from the transport line 33, and estimates an optimum dilution ratio by observing the color and density of the specimen, and input the estimated dilution ratio in the display column 655.

In the present embodiment, an a dilution ratio with a high possibility of being optimum is stored as a default (original ratio) dilution ratio in the default dilution DB 61a when measuring the specimen of a healthy subject or subject with light symptoms of illness by providing a default dilution DB 61a and original over original dilution ratio DB 61c in the control part 61 of the diagnostic information processing apparatus 60, and a dilution ratio with a high possibility of being optimum is stored as an over original dilution ratio (a default ratio of 10-fold or higher in the present embodiment) is stored in the over original dilution ratio DB 61c when measuring specimens of subjects with symptoms of severe illness. Accordingly, in the case of a healthy subject or subject with light symptoms, and even new patients (subjects) for whom there are no past measurement values, the default (original) dilution ratio becomes an optimum dilution ratio, and in the case of subjects with severe symptoms of disease, there is a high possibility that only one or two measurements will be needed to determine an optimum dilution ratio since the over original dilution ratio becomes the optimum dilution ratio. Thus, in the present embodiment, the number of measurements required to determine an optimum dilution ratio is reduced.

Furthermore, in the present embodiment, when the over original dilution ratio stored in the over original dilution DB 61c is 10-fold or higher than the default original ratio) dilution ratio stored in the default dilution DB 61a, and the measurement value measured at the default dilution ratio is greater than the upper limit value corresponding to the default dilution ratio, the control part 61 determines the over original dilution ratio as the next dilution ratio, and when next measuring a specimen that has a concentration greater than the default dilution ratio stored in the default dilution ratio DB 61a, the specimen is processed at an over original dilution ratio that is 10-fold or higher than the default dilution ratio as an optimum dilution ratio, such that there is a possibility that the measurement value will be within a measurable range. Therefore, the number of measurements required to determine an optimum dilution ratio is reduced.

In the present embodiment, since a next dilution ratio is associated and stored with information stored in a subject DB 61b by providing a subject DB 61b for associating and storing a next dilution ratio determined by the control part 61 with a subject ID and past measurement values, and controlling the sample preparation part 43 so as to process a specimen at a next dilution ratio stored in the subject DB 61b when performing a next measurement of a specimen of a subject who provided the specimen, the control part 45 reads the next dilution ratio based on the information stored in the subject DB 61b when subsequently measuring a specimen provided by the subject.

Since a determined next dilution ratio can be confirmed and modified by a technician by providing a display column (entry column) 655 for displaying a modifiable next dilution ratio determined by the control part 61, the technician can set an optimum next dilution ratio that corresponds to the specimen characteristics (color, viscosity, pathological condition of the subject providing the specimen and the like)

The present embodiment disclosed herein should not be construed as being limited in any way by this description which only provides examples. The scope of the present invention is expressed by the scope of the claims and not in any way by the description of the embodiments. Furthermore, equivalences in meaning with the scope of the claims and all modifications are included within the scope of the invention.

For example, in the present embodiment, a lowest level dilution ratio within the measurable range of a measurement value may be calculated from the measurement values obtained at the over original dilution ratio, and set as the next dilution ratio. Thus, the dilution ratio of a next measurement can be optimized even further.

Although examples have been described in which an analyzer makes a determination of an over upper limit (lower limit) scale anomaly when a measurement value obtained by an analyzer is greater that (less than) an upper limit (lower limit) stored in an upper limit and lower limit DB of the analyzer in the present embodiment, the present invention is not limited to this arrangement inasmuch as a determination as to whether or not a measurement value obtained by an analyzer is an over upper limit (lower limit) scale anomaly also may be made on the diagnostic information processing apparatus side.

Although examples have been described in which a host computer and two analyzers are connected with the diagnostic information processing apparatus via a communication line in the present embodiment, the present invention is not limited to this arrangement inasmuch as a client computer may be connected to the diagnostic information processing apparatus such that the diagnostic information processing apparatus may be operated from the client computer.

Although examples have been described in which the barcode of a barcode label adhered to a test tube includes information such as specimen number, date and exam type and the like in the present embodiment, the present invention is not limited to this arrangement inasmuch as subject identification information (subject ID) may be included beforehand in the barcode of the barcode label, such that a next dilution ratio corresponding to the read subject identification information (subject ID) may be provided to the sample preparation part (specimen dilution part).

Although examples have been described in which a subject DB (refer to FIG. 3) is configured by one table in the present embodiment, the present invention is not limited to this arrangement inasmuch as the subject DB also may be configured by two tables including a table associating a subject ID and a nest dilution ratio, and a table associating a subject ID and a specimen number.

Although examples have been described in which an over original dilution ratio for each item stored in an over original dilution DB 61c is 10-fold or greater than a default dilution ratio in all cases in the present embodiment, the present invention is not limited to this arrangement inasmuch as a dilution ratio less than 10-fold of a default dilution ratio for each item may be stored in the over original dilution DB 61c.

Although an enzyme immunoassay apparatus is used as the analyzer 40 and 50 in the present embodiment, the present invention is not limited to this arrangement inasmuch as another analyzer such as a biochemical analyzer, urine analyzer and the like may be used as the analyzer 40.

Figure 13:
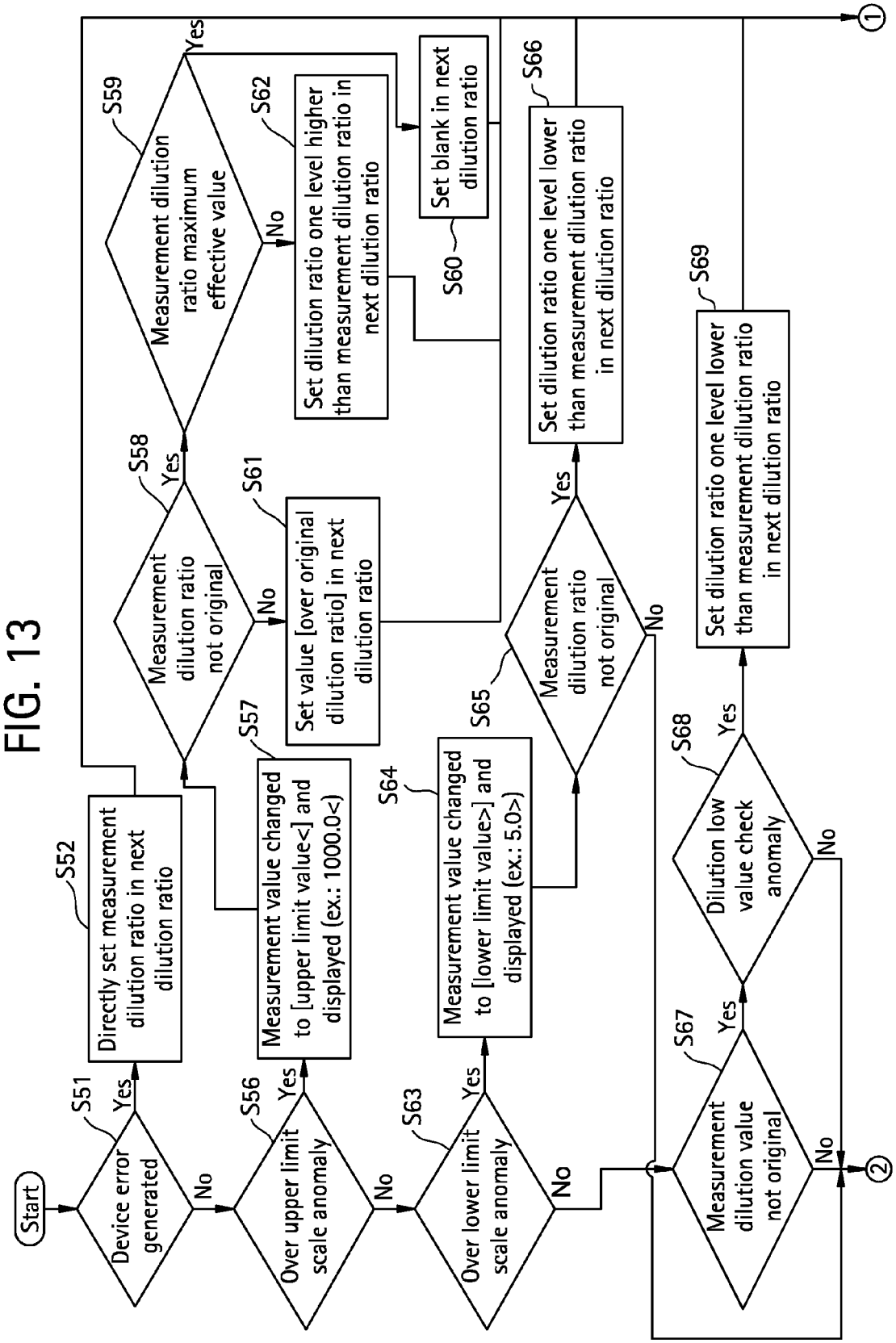
FIG. 13 is a flow chart showing details (subroutines) of the data check process performed by the diagnostic information processing apparatus of the embodiment of the analysis system shown in step S37 of FIG. 11.
Figure 16:
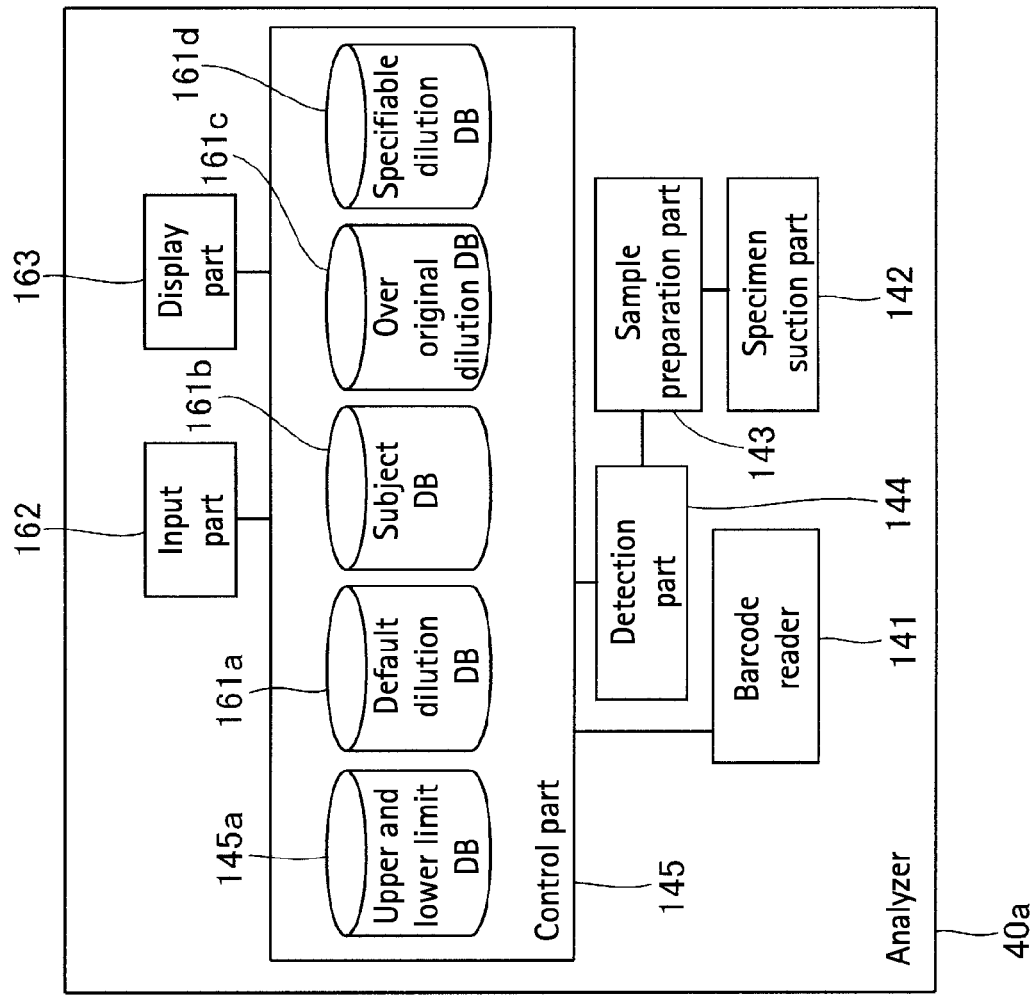
FIG. 16 is a block diagram showing a modification of the analyzer of the analysis system of the embodiment shown in FIG. 1.

Although examples have been described in the above embodiment in terms of separately providing a control part 61 including a default dilution DB 61a, subject DB 61b, over original dilution ratio DB 61c, and specifiable dilution DB 61d, and an analyzer 40 provided with a barcode reader 41, specimen suction part 42, sample preparation part 43, detection part 44, and control part 45 including an upper and lower limit DB 45a and a diagnostic information processing apparatus 60 provided with an input part 62 and display part 63, the present invention is not limited to this arrangement inasmuch as a detection part 144, sample preparation part 143, specimen suction part 142, barcode reader 141, display part 163, input part 162, and control part 145 including a upper and lower limit DB 145a, default dilution DB 161a, subject DB 161b, over original dilution DB 161c and specifiable dilution DB 161*d* may all be incorporated in a single analyzer (analysis system) 40*a*, shown in the modification of FIG. 16, such that the control part 145 executes the data check processes shown in FIGS. 13 through 15.

What is claimed is:

1. An analyzing system, comprising:
   an analyzer for measuring a sample based on a designated dilution parameter;
   a memory for storing a first dilution parameter, indicating no dilution, which is used as a default parameter and a second dilution parameter which is different from the first dilution parameter and can be supplied by a user of the analyzing system;
   a retriever for retrieving one of the first dilution parameter and the second dilution parameter as a next dilution parameter from the memory based on a measurement result of the sample; and
   a transmitter for transmitting the retrieved next dilution parameter to the analyzer;
   wherein the retriever retrieves the second dilution parameter when the first dilution parameter is not suitable for measuring the sample.

2. The analyzing system of claim 1, further comprising an input device for inputting the second dilution parameter by the user of the analyzing system.

3. The analyzing system of claim 1,
   wherein the memory stores the next dilution parameter retrieved by the retriever and a corresponding subject identifying information for identifying a subject who offered the measured sample; and
   the transmitter transmits the next dilution parameter to the analyzer based on the subject identifying information stored in the memory.

4. The analyzing system of claim 1,
   wherein the retriever does not retrieve any dilution parameter when the greatest dilution parameter stored in the memory is not great enough for measuring the sample.

5. The analyzing system of claim 1, further comprising a verifying means for verifying the measurement result.

6. The analyzing system of claim 1, further comprising a dilution ratio check means for checking whether the designated dilution parameter is too great based on the measurement result of the sample and a dilution parameter used for the measured sample.

7. The analyzing system of claim 1, further comprising a display for displaying the next dilution parameter which can be changed by the user of the analyzing system via the display.

8. The analyzing system of claim 7,
   wherein the next dilution parameter can be changed only to predetermined parameters.

9. A diagnostic information processing device connected to an analyzer for measuring a sample based on a designated dilution parameter, comprising:
   a memory for storing a first dilution parameter, indicating no dilution, which is used as a default parameter and a second dilution parameter which is different from the first dilution parameter and can be supplied by a user of the diagnostic information processing device;
   a retriever for retrieving one of the first dilution parameter and the second dilution parameter as a next dilution parameter from the memory based on a measurement result of a sample; and
   a transmitter for transmitting the retrieved next dilution parameter to the analyzer;
   wherein the retriever retrieves the second dilution parameter when the first dilution parameter is not suitable for measuring the sample.

10. The diagnostic information processing device of claim 9, further comprising an input device for inputting the second dilution parameter by the user of the analyzing system.

11. The diagnostic information processing device of claim 9, wherein the memory stores the next dilution parameter retrieved by the retriever and a corresponding subject identifying information for identifying a subject who offered the measured sample; and
   the transmitter transmits the next dilution parameter to the analyzer based on the subject identifying information stored in the memory.

12. The diagnostic information processing device of claim 9, wherein the retriever does not retrieve any dilution parameter when the greatest dilution parameter stored in the memory is not great enough for measuring the sample.

13. The diagnostic information processing device of claim 9 further comprising a verifying means for verifying the measurement result.

14. The diagnostic information processing device of claim 9, further comprising a dilution ratio check means for checking whether the designated dilution parameter is too great based an the measurement result of the sample and a dilution parameter used for the measured sample.

15. The diagnostic information processing device of claim 9, further comprising a display for displaying the next dilution parameter which can be changed by the user of the analyzing system via the display.

16. The diagnostic information processing device of claim 15, wherein the next dilution parameter can be changed only to predetermined parameters.

17. A computer program product for processing diagnostic information, comprising:
   a computer readable medium; and
   computer instructions, on the computer readable medium, for enabling a computer to perform the operation of:
     storing a first dilution parameter, indicating no dilution, which is used as a default parameter and a second dilution parameter which is different from the first dilution parameter and can be supplied by a user of the computer;
     retrieving one of the first dilution parameter and the second dilution parameter as a next dilution parameter based on a measurement result of a sample; and
     transmitting the retrieved next dilution parameter to an analyzer;
     wherein the second dilution parameter is retrieved when the first dilution parameter is not suitable for measuring the sample.

* * * * *